United States Patent
Haras

(10) Patent No.: US 8,295,913 B2
(45) Date of Patent: Oct. 23, 2012

(54) METHOD AND DEVICE FOR PLANNING AND/OR MONITORING AN INTERVENTIONAL HIGH-FREQUENCY THERMOABLATION

(75) Inventor: Gabriel Haras, Muecke (DE)

(73) Assignee: Siemens Aktiengesellschaft, Munich (DE)

( * ) Notice: Subject to any disclaimer, the term of this patent is extended or adjusted under 35 U.S.C. 154(b) by 705 days.

(21) Appl. No.: 12/266,721

(22) Filed: Nov. 7, 2008

(65) Prior Publication Data

US 2009/0124896 A1 May 14, 2009

(30) Foreign Application Priority Data

Nov. 9, 2007 (DE) .......................... 10 2007 053 394

(51) Int. Cl.
*A61B 5/05* (2006.01)
(52) U.S. Cl. ........................ 600/427; 600/425
(58) Field of Classification Search .................. None
See application file for complete search history.

(56) References Cited

U.S. PATENT DOCUMENTS

| 6,241,725 B1 * | 6/2001 | Cosman .......................... 606/41 |
| 6,575,969 B1 | 6/2003 | Rittman, III et al. |
| 2002/0111615 A1 * | 8/2002 | Cosman et al. .................. 606/41 |
| 2006/0004275 A1 * | 1/2006 | Vija et al. ....................... 600/407 |
| 2007/0167706 A1 | 7/2007 | Boese et al. |
| 2009/0118613 A1 * | 5/2009 | Krugman et al. ............. 600/431 |

FOREIGN PATENT DOCUMENTS

WO   WO 02/089686   11/2002

* cited by examiner

*Primary Examiner* — Long V. Le
*Assistant Examiner* — Bo J Peng
(74) *Attorney, Agent, or Firm* — Schiff Hardin LLP

(57) ABSTRACT

In a method as well as a device for planning and/or monitoring an interventional high-frequency thermoablation, 3D image data of a region (1) of interest of a body are acquired with a tomographical imaging apparatus and are presented on an image display device. In the method, a database is provided in which, for at least one interventional instrument available for high-frequency thermoablation, a volume region for at least one high-frequency power generable with the instrument is established in which a thermoablation is achieved in a tissue with the instrument at this high-frequency power. Upon marking at least one ablation position in the image representations, a 3D object representing the volume region or a volume region derived from this is then mixed in at least semi-transparently at this ablation position. The method and the associated device enable a better planning and monitoring of an interventional high-frequency thermoablation by the user.

8 Claims, 2 Drawing Sheets

METHOD AND DEVICE FOR PLANNING AND/OR MONITORING AN INTERVENTIONAL HIGH-FREQUENCY THERMOABLATION

BACKGROUND OF THE INVENTION

1. Field of the Invention

This present invention concerns a method for planning and/or monitoring an interventional high-frequency thermoablation, in which method 3D image data of a region of interest of a body are acquired with a tomographical imaging apparatus and are presented on an image display device so that a target area for the thermoablation as well as an extent of the target area are recognizable in one or more image presentations of the 3D image data. The invention also concerns a device for implementation of the method.

2. Description of the Prior Art

Interventional procedures are frequently supported by imaging techniques that enable a monitoring of the positioning of the instruments inserted into the body. Particular tomographical imaging methods such as computer tomography (CT) offer advantages both in the monitoring of the procedure and in the preceding planning based on the available 3D image data. For example, probes, biopsy needles or other medical instruments can be navigated to a specific target point in the body with the assistance of computer tomography. A special field of use is high-frequency (HF) thermoablation. In this technique, a needle-shaped applicator is penetrated into the body with local anesthetization and is pushed to the location of a tumor under CT monitoring. If the applicator is located in the target area, thermal energy is applied that leads to the destruction of the tumor tissue.

The extent of the ablated area depends on, among other things, the application duration as well as the power of the applicator. The applicator required for tumor ablation is normally determined in advance in a planning step. The tumor size and shape are thereby evaluated using CT image data that were acquired in advance from the region of interest of the body of the patient. After the user has determined the size of the tumor, he can select the applicator using data sheets and tables.

Modern ablation devices can measure the temperature and the impedance at the probe head during the ablation and therefore can control the ablation. An end point of the application can also be detected since the impedance normally drops off quite steeply when the tissue dies.

For the user, in the planning and during an intervention it is very difficult to estimate, by paging through an available 3D image data set, whether the target area which should be treated with the RF thermoablation is also sufficiently encompassed. This problem is present both in the planning phase and during the intervention. A particular difficulty is posed by larger tumors that cannot be treated with a single applicator position but rather in which the applicator must be brought to multiple ablation positions in succession in order to completely encompass the tumor.

SUMMARY OF THE INVENTION

An object of the present invention is to provide a method for planning and/or monitoring an interventional high-frequency thermoablation with which an improved planning and/or monitoring of the thermoablation is enabled for the user.

The above object is achieved in accordance with the present invention by a method and a device for planting and/or monitoring an interventional high-frequency thermal ablation, wherein #d image date of a region of interest of a body are acquired with a tomographical imaging apparatus and are presented on an image display device so that a target area of the thermal ablation, as well as an extent of the target area, are recognizable in one or more image representations of the 3D image data, and wherein a database is provided in which, for at least one interventional instrument available for the high-frequency thermal ablation, a volume region for at least one high-frequency power that can be generated with the instrument is established, in which thermal ablation is achieved in tissue with the instrument at this high-frequency power. Upon marking at least one actual or planned ablation position of the instrument in the image representation or representations, a 3D object representing the volume region, or a volume region derived therefrom, is then mixed into the displayed image, at least semi-transparently, at this ablation position.

In the inventive method, 3D image data of a region of interest of a body are acquired with a tomographical imaging apparatus and are presented on an image display device so that a target area for the thermoablation as well as an extent of the target area are recognizable in one or more image representations of the 3D image data. For this purpose, a computed tomography or x-ray C-arm apparatus or a magnetic resonance tomograph with which the tomographical 3D image data of the region of interest are acquired is advantageously used. The image representations based on said 3D image data are advantageously correspondingly rendered representations that have been generated by means of VRT (volume rendering technique) or MPR (multi-planar reformatting), for example. Furthermore, it is naturally additionally or alternatively also possible to define suitable slice planes that are then presented to the user as slice images on the image display device. The display software is advantageously designed so that the user can interactively, arbitrarily rotate the image presentations in order to obtain the suitable perspective.

In the inventive method, a database is provided in which, for at least one interventional instrument available for the intervention for high-frequency thermoablation (i.e. an ablation device with corresponding applicator), a volume region for at least one high-frequency power generable with the instrument is established in which a thermoablation is achieved in a tissue with the instrument at this high-frequency power. Upon marking at least one actual or planned ablation position of the instrument in the image representation or representations (advantageously with a graphical input device), a 3D object representing the volume region or a volume region derived from this is then mixed in at this marked ablation position, at least semi-transparently. The marking advantageously ensues with a graphical input device (for example with a mouse) with which the user clicks on the ablation position selected by him in the image representation. If the method is used not only for planning but also for monitoring of an interventional high-frequency thermoablation, the 3D image data of the region of interest are acquired at least once during the intervention. The tip of the applicator, which the user can mark as an ablation position in the image representations, is then to be detected in the corresponding image representations.

The database is advantageously fashioned so that the stored object shapes of the 3D objects can be modified by the user and/or so that the user can expand the database with additional object shapes. For example, a modification of the 3D objects can ensue interactively via provision of a graphical tool with which the user can manipulate a shown object shape on the screen. The database should advantageously also enable a simple exchange of stored object forms with other databases for such object forms.

The 3D object that is at least semi-transparently mixed into the image representation(s) can be a geometrically simple object, for example a sphere, an ellipsoid or a pear- or lobe-shaped object. In this case, the radius of the sphere or pear or, respectively, lobe or the length of the semiaxes of the ellipsoid can then be defined in the database for each high-frequency power or for each instrument. However, arbitrary three-dimensional shapes with regard to each HF power and/or each instrument can also be directly defined that are then mixed into the corresponding stored three-dimensional shape in the image representation. This enables a mixing of the achievable volume regions even with commercially available probe shapes of applicators that do not necessarily cover a spherical or ellipsoidal area. As used herein, the term "database" encompasses any structured collection of data that belong together in terms of content and are connected with one another, which collection can be accessed by means of electronic data processing. The structure of the database, for example in the form of a table or more complex data linkages, is hereby insignificant.

In a further embodiment, a shield-shaped object is also mixed into the image representation given use of corresponding applicator types. This shield-shaped object represents the wires spread out in approximately a shield shape at the tip of this applicator type.

Due to the translucent overlay of the anatomical information visible in the image representations with the 3D object that indicates the range achieved by the instrument at the corresponding HF power given marking of an ablation position, the user can immediately recognize whether the target area (for example the tumor) is encompassed with these parameters. In an embodiment for planning the examination, the user can simply just click in the center of the tumor and then sees, using the translucent, overlaid region, whether the entire tumor is detected and how large a possible safety margin is. Especially given the treatment of larger tumors, multiple ablation positions can thus be defined relatively simply in order to enlarge the encompassed area. By the ablation position, what is thereby to be understood is the position at which the tip of the applicator is located upon application of the RF radiation. The user thus is no longer dependent on his or her own estimation that is based solely on his or her experimental values. In particular, upon paging through the data set the user recognizes immediately (due to the mixed-in contours of the 3D object on each slice image) whether and to what extent the target area in this slice is encompassed by the applicator.

The database advantageously contains data for multiple different instruments for high-frequency thermoablation. The users then select the suitable instrument and can have the corresponding volume regions displayed in the event that multiple instruments for the procedure are available.

The volume region defined in the database can apply exactly for only specific tissue properties. This is normally sufficient for the planning and monitoring of an intervention and in every case offers significant advantages relative to a subjective estimation by the user. Theoretical calculation models that can simulate a heat propagation in tissue are presently in development. Naturally, the inventive method as well as the associated device can also be used with such a software that calculates a volume region for a target tissue from the volume region of the reference tissue or other information about the thermoablation properties of the applicator and data about the composition and structure of said target tissue, in which calculation the dissipation of the heat by vessels through which blood flows can also be taken into account. In the method this requires an intermediate step between the fetching of the volume region and the presentation of the 3D object in the image representation.

In an embodiment of the method, a first ablation position marked in the image representations is connected with a second ablation position marked in the image representations by a straight line that is extended outwards to the surface of the shown body. The two marked ablation positions therefore lie on a straight line that corresponds to a possible penetration channel for the instrument. If one of the two 3D objects that are mixed in at the two ablation positions is interactively shifted by the user, the connection line as well the other object follow correspondingly. A 3D object (in particular in the form of a sphere) can hereby also be additionally mixed in at the intersection point of the straight line with the body surface, corresponds to the penetration point. This 3D object then also follows a corresponding shift. Suitable methods that can calculate this boundary line or boundary surface from the image data (for example via threshold methods) are already available for the detection of the surface of the body in the 3D image data. The user can therefore shift the 3D objects back and forth in the image representation until the entire target area is encompassed and the penetration channel no longer runs through critical or impassible areas.

In another embodiment, the mutual separation of these ablation positions as well as optionally the distance of one or both ablation positions from the body surface are also determined on the straight line from the 3D image data and the marked ablation positions and are output. These separations then correspond to the distances over which the user must retract the inserted instrument in order to arrive from one ablation position to the other. The distance to the penetration point informs the user (possibly together with the separations of the two ablation positions) about the maximum distance that the instrument must be inserted into the patient, and thus about the minimum required length of the instrument that is necessary for the procedure.

The inventive method and device can also be advantageously used during an intervention in order to monitor the intervention. The exact positioning of the instrument for thermoablation has generally not been achieved. By the acquisition of a 3D image data set after a positioning of the instrument at one ablation position, however, the user can detect the tip of the instrument in the image representations. The user can then monitor whether the present position of the instrument is acceptable for the planned thermoablation, in that he clicks on the tip of the instrument in the image representation or otherwise marks this in the image representation. The volume region with the 3D object that is encompassed given this ablation position of the instrument is thereupon displayed to him for this instrument and the set RF power. The user thus can check whether, in spite of a possibly sub-optimal position of the instrument, the tumor is still completely encompassed. This can naturally also ensue for multiple ablation positions.

In a further embodiment, the detection of the tip of the instrument ensues automatically via an image processing algorithm, wherein the volume region detected by the instrument is then also automatically displayed at the detected position with the 3D object. Suitable image processing algorithms to localize the position of the tip of instruments in medical image data are known.

The inventive device for planning and/or monitoring an interventional high-frequency thermoablation comprises at least one memory unit; one image display unit with an image display device and a graphical input device; and a database. In the database, for at least one interventional instrument for high-frequency thermoablation, a volume region for at least one high-frequency power generable with said instrument is established in which a thermoablation in a tissue is achieved with the instrument at this high-frequency power. The image display unit, which naturally must also contain a corresponding microprocessor for calculations, is fashioned so that it can present on the image display device tomographical 3D image data of a region of interest of a body that are stored in the memory unit so that a target area for a thermoablation as well as an extent of the target area are recognizable in one or more image representations of the 3D image data. The image display unit is furthermore fashioned so that, given marking of at least one ablation position of the instrument with the graphical input device in the image representation or representations, it mixes a 3D object representing the volume region (or a volume region derived from said 3D object) in at least semi-transparently at this ablation position. The device can be fashioned as a separate system or can be connected with the tomographical imaging apparatus (for example a computed tomography apparatus).

In the preferred embodiments the device is fashioned for the implementation of the automated method steps of the method explained in the preceding according to its different embodiments. This primarily pertains to the image display unit, in which the listed steps are executed.

In another embodiment of the device and of the method, the image display unit also contains: a segmentation module that automatically segments the target area as well as the extent of the target area in the 3D image data; as well as an adaptation module that automatically determines one or more ablation positions on the basis of the volume regions and the segmented target area defined in the database, with which one or more ablation positions the target area is completely encompassed. The determined ablation positions are then automatically marked by this adaptation module in the one or more image representations, such that the 3D objects corresponding to the volume regions are automatically mixed in. The user can then check whether the automatically selected ablation positions correspond to his ideas, and if necessary can still interactively shift the mixed-in 3D objects. Suitable segmentation methods for segmentation of anatomical subjects in 3D image data are known to those skilled in the art. For the localization of suitable ablation positions, via (for example) successive displacement of the ablation position and geometric comparisons between the corresponding 3D objects and the segmented image data it must be achieved that the segmented target area lies completely within the respective 3D object. Known techniques of error minimization can be used for this purpose.

With the described method and the associated device it is possible to also plan and treat larger target areas (in particular tumors) with only one instrument or, respectively, one probe and a single penetration channel. A particular advantage lies in the lower stress of the patient since only a single penetration channel is worked with and fewer monitoring scans are required for probe positioning. With the use of computed tomography systems, this also entails a lower radiation exposure and significantly improves the workflow. The procedure is significantly faster and simpler via the method. A particular advantage of the method and the device is that the user can therefore position the applicator in a controlled manner. This increases the safety for the user and for the patient.

Although the present method and the associated device are described primarily for CT-assisted interventional procedures, it is also possible to use other apparatuses for tomographical imaging (for example a magnetic resonance tomography apparatus) as an imaging apparatus.

DESCRIPTION OF THE PREFERRED EMBODIMENTS

Figure 1:
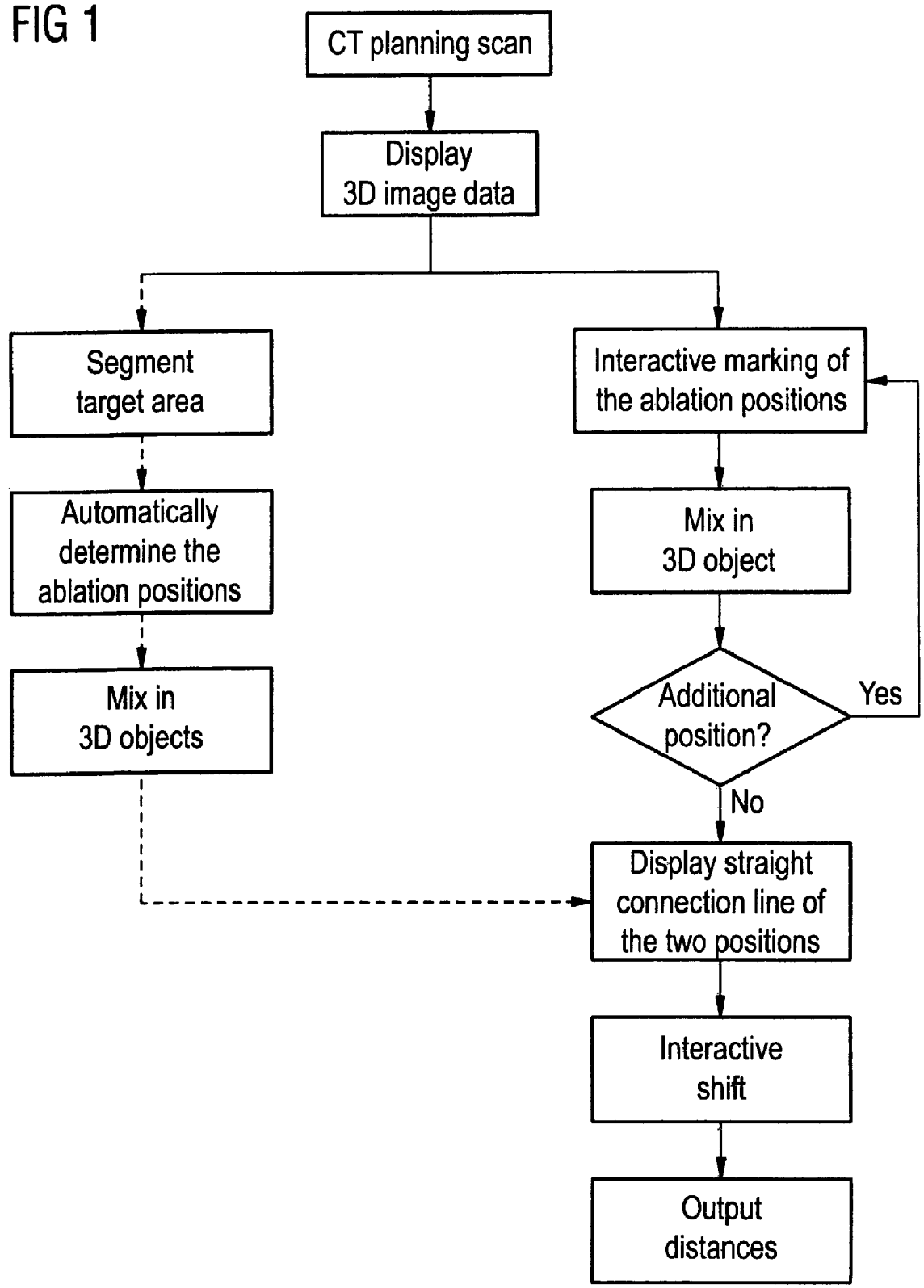
FIG. 1 shows an exemplary workflow diagram for the implementation of a CT-controlled RF thermoablation with the inventive method and the inventive device.

The inventive method is explained again using the flow diagram as an example in FIG. 1. In order to be able to bring the inserted HFA probe (HFA: high-frequency thermoablation) into the correct position, immediately before the procedure for tumor ablation a planning scan of the patient is conducted with a computer tomograph in order to acquire the planning data. A three-dimensional CT image data set of the patient is thereby generated. The 3D image data can be viewed on a suitable CT console. The data set can be interactively, arbitrarily rotated by the user. The user defines suitable slice planes until the tumor is visibly well prepared in the image representations.

The user marks a position within the tumor around which a 3D object that corresponds to the effective radius of the inserted HFA probe is mixed in. This 3D object is translucently overlaid on the anatomical information in the image representations. The user now recognizes (for example in the image representation) that the effective radius of this probe is not sufficient to entirely encompass the tumor. The user thereupon marks within the target area a second ablation position at which a 3D object is again mixed in that corresponds to the effective radius of the inserted HFA probe. The system connects the two ablation positions with a straight line and extends this line up to the patient surface. The user then shifts the connected objects until the entire tumor is encompassed and the penetration channel no longer runs through critical or impassible areas. By mixing the 3D objects into the image representation, the user, upon paging through the data set, can immediately recognize in each representation whether the tumor is still encompassed by the applicator. A particular presentation capability is not required for this.

Figure 2:
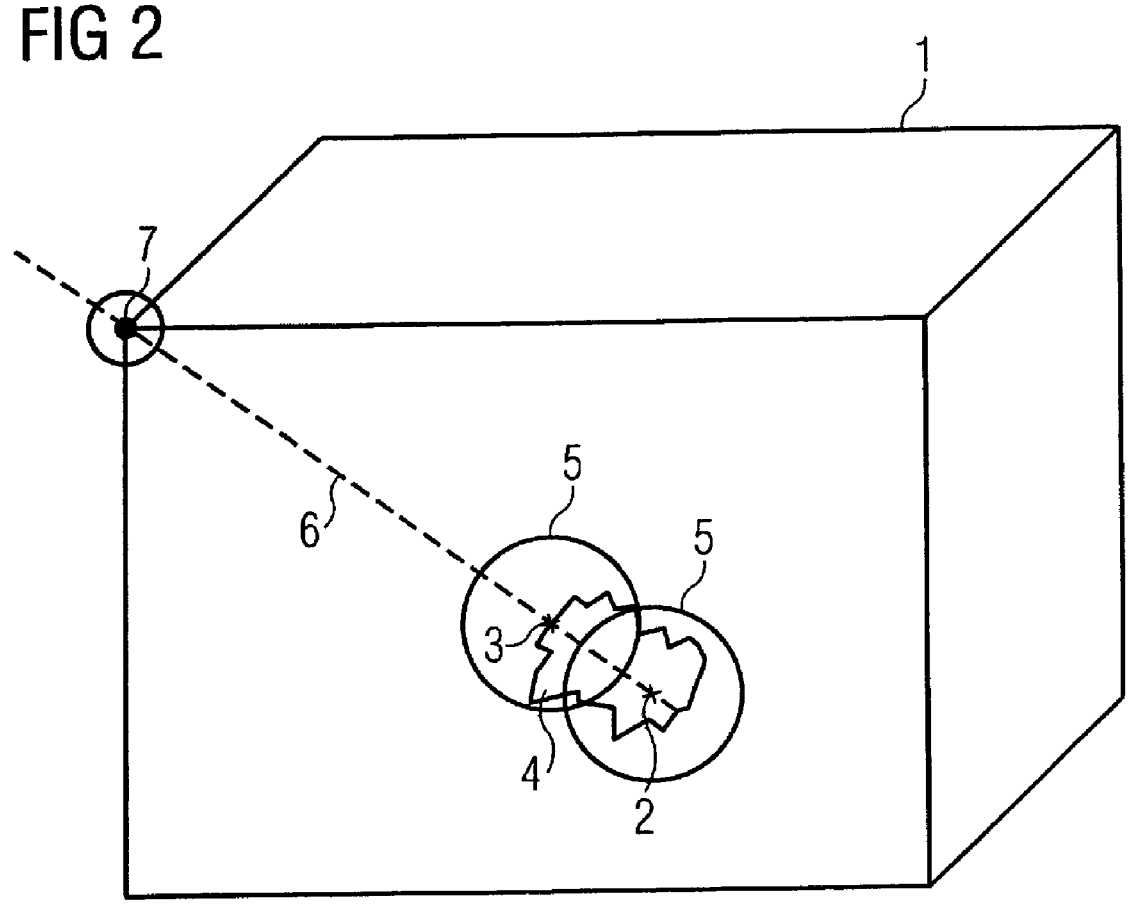
FIG. 2 is a schematic image representation to illustrate the mixing of 3D objects and the penetration channel in accordance with the invention.

FIG. 2 shows with significantly schematization a corresponding representation in which a first ablation position 2 and a second ablation position 3 are marked in a body region 1 of interest. The tumor 4 is likewise indicated in this image representation. 3D objects 5 that represent the effective radius of the inserted probe around these ablation positions are placed around these two positions. The two ablation positions are connected by a straight line 6 that runs up to the patient surface and there defines a penetration point 7. By shifting one of the mixed-in objects 5 or the penetration point 7, the corresponding other objects 5 and the straight line 6 shift as well. The user can thus conduct an optimal planning of the ablation.

The intervention can subsequently be started. The user hereby positions the HFA probe at the first ablation position 2 and conducts CT monitoring scans for this. Using the 3D image data hereby acquired, the user respectively checks in the current image data whether the probe position for ablation position 2 and ablation position 3 is all right and corrects the probe position if necessary. The therapy at ablation position 2 is subsequently conducted and the probe is retracted by the automatically calculated distance. The therapy at the ablation position 3 follows after this. After the end of this ablation, the probe is extracted. The procedure is ended.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for planning and/or monitoring an interventional high-frequency thermal ablation, comprising the steps of:

acquiring 3D image data of a region of interest of a body with a tomographical imaging apparatus and displaying an image represented by said 3D image data at a display device, said 3D image data and the displayed image comprising a target area for a thermal ablation and an indication of a spatial extent of said target area;

providing a database to store at least one interventional instrument available for implementing said thermal ablation, and to store data representing a volume region in which thermal ablation is achieved in tissue with the instrument for at least one high-frequency power that can be generated with the instrument;

marking at least one marked position in the displayed image, selected from the group consisting of an actual position of the instrument or a planned ablation position of the instrument;

upon marking said marked position, automatically mixing a 3D object, representing said volume region or a derived volume region that is derived from said volume region, in the displayed image and representing said 3D object at least semi-transparently at the ablation position in the displayed image;

marking at least two different marked positions in said image, each marked position representing a position at which a high-frequency thermal ablation is to occur, and mixing respective 3D objects into said image representing the volume regions for each of said marked positions, and automatically connecting said ablation positions with a straight connecting line in said 3D image data that extends to an exterior surface of the body, to thereby define a penetration channel, and displaying said penetration channel in said image at said display device; and manually interactively shifting the mixed-in 3D objects in said image at said display device using a graphical input tool that interacts with said display device, and automatically modifying said straight line connection to follow said shifting.

2. A method as claimed in claim 1 comprising marking said marked position using a graphical input apparatus that interacts with said display device.

3. A method as claimed in claim 1 comprising marking said marked position as the actual ablation position, and generating the marking of the actual ablation position using a computerized image processing algorithm that automatically detects a position of a tip of the instrument in said 3D image data.

4. A method as claimed in claim 1 comprising manually interactively manipulating the 3D object mixed into the displayed image using a graphical input tool that interacts with said image display device to ultimately place said 3D object at a manipulated position in said image, and storing said manipulated position in said database.

5. A method as claimed in claim 1 comprising:

storing, in said database, a plurality of different volume regions for said interventional instrument that represent tissue ablation regions for respectively different powers at which said interventional instrument is operable; and allowing selection of one of said powers via a menu displayed at said display device, as a selected power, and wherein the step of mixing a 3D object into said image comprises mixing a 3D object into said image that represents the volume region associated with the selected power.

6. A method as claimed in claim 1 comprising automatically determining a distance between said two ablation positions and generating a visual indication of said distance at said display device.

7. A method as claimed in claim 6 comprising automatically determining a distance between one of said ablation positions and said exterior surface of the body on said straight connecting line, and displaying an indication of said distance between said at least one of the ablation positions and the exterior surface of the body at said display device.

8. A method as claimed in claim 1 comprising, using an automated image segmentation algorithm, segmenting said target area in said 3D image data and automatically determining at least one ablation position in which said target area is completely encompassed, dependent on said volume region defined in said database and said segmented target area, and automatically marking the determined ablation position in said image at said display device.

* * * * *